United States Patent
Chau et al.

(10) Patent No.: US 10,722,534 B2
(45) Date of Patent: Jul. 28, 2020

(54) MAGNETIC NANOAGGREGATE-EMBEDDED BEAD, MANUFACTURING METHOD THEREOF AND BIOPARTICLE DETECTION METHOD USING THE SAME

(71) Applicant: National Chung Cheng University, Chiayi (TW)

(72) Inventors: Lai-Kwan Chau, Chiayi (TW); Shih-Ying Yen, Kaohsiung (TW)

(73) Assignee: National Chung Cheng University, Chia-Yi (TW)

( * ) Notice: Subject to any disclaimer, the term of this patent is extended or adjusted under 35 U.S.C. 154(b) by 322 days.

(21) Appl. No.: 15/648,102

(22) Filed: Jul. 12, 2017

(65) Prior Publication Data
US 2018/0200296 A1   Jul. 19, 2018

(30) Foreign Application Priority Data
Jan. 19, 2017   (TW) .............................. 106101977 A

(51) Int. Cl.
| | |
|---|---|
| *B82Y 5/00* | (2011.01) |
| *A61K 33/38* | (2006.01) |
| *A61K 47/69* | (2017.01) |
| *A61K 38/02* | (2006.01) |
| *A61K 47/52* | (2017.01) |
| *G01N 33/543* | (2006.01) |

(Continued)

(52) U.S. Cl.
CPC .............. *A61K 33/38* (2013.01); *A61K 38/02* (2013.01); *A61K 47/52* (2017.08); *A61K 47/6923* (2017.08); *A61K 47/6929* (2017.08); *G01N 33/54326* (2013.01); *G01N 33/585* (2013.01); *A61K 33/00* (2013.01); *B82Y 5/00* (2013.01); *Y02A 50/481* (2018.01)

(58) Field of Classification Search
None
See application file for complete search history.

(56) References Cited

U.S. PATENT DOCUMENTS

| | | | |
|---|---|---|---|
| 2009/0130655 A1* | 5/2009 | Chau ..................... | B82Y 15/00 435/5 |
| 2011/0182815 A1* | 7/2011 | Daich .................. | A61K 49/085 424/9.1 |

OTHER PUBLICATIONS

Chon et al., "Simultaneous immunoassay for the detection of two lung cancer markers using functionalized SERS nanoprobes", The Royal Society of Chemistry, ChemComm, 47, 2011, pp. 12515-12517. (Year: 2011).*

* cited by examiner

*Primary Examiner* — Rebecca M Giere
(74) *Attorney, Agent, or Firm* — Wang Law Firm, Inc.

(57) ABSTRACT

A magnetic nanoaggregate-embedded bead (NAEB), a manufacturing method thereof and a bioparticle detection method using the same are disclosed. The magnetic NAEB has a protective nanoshell, noble metal nanoparticles, Raman reporter molecules and at least one magnetic nanoparticle. The protective nanoshell covers the noble metal nanoparticles, the Raman reporter molecules and the at least one magnetic nanoparticle. The noble metal nanoparticles, the Raman reporter molecules and the at least one magnetic nanoparticle form a magnetic nanoaggregate. Preferably, a chemical modification is performed on the magnetic NAEB, such that at least one targeting molecule is formed on an outer wall of the protective nanoshell, wherein a type of the targeting molecule is corresponding to a type of the bioparticle to be detected.

18 Claims, 7 Drawing Sheets

(51) Int. Cl.
*G01N 33/58* (2006.01)
*A61K 33/00* (2006.01)

MAGNETIC NANOAGGREGATE-EMBEDDED BEAD, MANUFACTURING METHOD THEREOF AND BIOPARTICLE DETECTION METHOD USING THE SAME

CROSS-REFERENCE TO RELATED APPLICATION

This application claims priority to and the benefit of Taiwan Patent Application No. 106101977, filed on Jan. 19, 2017, in the Taiwan Intellectual Property Office, the entire content of which is incorporated herein by reference.

BACKGROUND OF THE INVENTION

1. Field of the Invention

The present disclosure relates to a nanoaggregate-embedded bead (NAEB) for detecting a bioparticle, in particular, to a magnetic NAEB, a manufacturing method thereof and a bioparticle detection method using the same.

2. Description of the Related Art

Food-borne diseases have received a lot of attention nowadays by World Health Organization (WHO), which not only affect people's health, but also relate to the cost of medical resources. Main pathogenic bacteria of food-borne diseases are bioparticles of Salmonella and E. coli. The conventional detection methods, such as enzyme-linked immunosorbent assay (ELISA) or polymerase chain reaction (PCR), generally require a pre-enrichment or selective enrichment step first and then perform the biotype test or serotype identification. The conventional detection methods are time-consuming and cumbersome, so scientists are still committed to the development of rapid screening methods for pathogens, and Salmonella is one of the important subject matters. Thus, a NAEB Raman tag is proposed to detect the bioparticle, and the bioparticle comprises bacteria, virus, or cell, such as Salmonella or circulating tumor cell.

The NAEB Raman tag is the combination of the molecules with strong Raman scattering characteristics (named Raman reporter molecules) and the metal nanoparticles. The adsorbed molecule at the surface of the metal nanoparticles is excited by a field generated by the incident light and the Raman scattering light. When there are resonances between the excitation and scattered fields and surface plasmons, electromagnetic field enhancement at the nanoparticle surface occurs and leads to enhancement of the Raman scattering signal. Through the plasmon resonance generated by metal nanoparticles, the surface-enhanced Raman scattering (SERS) spectrum of the Raman reporter molecules can be obtained. Furthermore, a hot spot is generated at the junction between the metal nanoparticles in the NAEB Raman tag, thus the field at the hot spot is enhanced dramatically, and the Raman signal produced by the adsorbed molecule at the hot spot is also increased dramatically. However, when using the NAEB Raman tag to detect the bioparticles without the background by the NAEB Raman tag itself, a separation step with the addition of magnetic nanoparticles is in general performed. Such an additional step makes the experimental procedures more cumbersome.

Additionally, the antibody molecules on the NAEB Raman tag and the magnetic nanoparticles will compete for the binding sites of the epitope group of the same type, and such binding sites may locate in close regions. Thus, the steric hindrance for binding may happen, and the number of available binding sites may decrease. Or alternatively, two different antibodies for two different epitope groups on the bioparticle may be separately conjugated on the NAEB Raman tag and the magnetic nanoparticles. However, some bioparticles may have only one epitope group.

SUMMARY

To solve at least one of the above technical problems, one objective of the present disclosure is to provide a magnetic NAEB, a manufacturing method thereof and a bioparticle detection method using the same.

According to at least one objective of the present disclosure, a magnetic NAEB is provided. The magnetic NAEB has a protective nanoshell, noble metal nanoparticles, Raman reporter molecules and at least one magnetic nanoparticle. The protective nanoshell is for example made of silica, polymer, or metal oxide such as titania and zirconia, and covers the noble metal nanoparticles, the Raman reporter molecules and the at least one magnetic nanoparticle. The noble metal nanoparticles can be gold nanoparticles or silver nanoparticles. The noble metal nanoparticles, the Raman reporter molecules, and the at least one magnetic nanoparticle form a magnetic nanoaggregate.

According to at least one objective of the present disclosure, a manufacturing method of the magnetic NAEB is provided. Firstly, noble metal nanoparticles, Raman reporter molecules and magnetic nanoparticles form magnetic nanoaggregates. Then, protective nanoshells cover the magnetic nanoaggregates.

According to one objective of the present disclosure, a bioparticle detection method using magnetic NAEBs is provided. Firstly, provide the magnetic NAEBs as mentioned above. Then a targeting molecule, such as antibody, aptamer, DNA, glycan, or chemical group, is conjugated on the surface of the magnetic NAEBs to provide the functionalized magnetic NAEBs. Next, make the magnetic NAEBs bind to one or more bioparticles. Utilize a magnetic component to attract the bioparticles bound with the magnetic NAEBs and the unbound magnetic NAEBs. Keep the portion of bioparticles bound with the magnetic NAEBs and the unbound magnetic NAEBs that has been attracted by the magnetic component. Utilize a filtering membrane to filter out the unbound magnetic NAEBs while the bioparticles bound with the magnetic NAEBs are kept on the filtering membrane. Utilize a Raman microscope to observe a SERS spectrum of the bioparticles bound with magnetic NAEBs which are left on the filtering membrane, so as to detect the bioparticles.

Accordingly, the magnetic NAEB, the manufacturing method thereof and a bioparticle detection method using the same may have one or more advantages as follows.

(1) The manufacturing cost of the magnetic NAEB is not high, thus having the low cost advantage.

(2) The magnetic NAEB consists of at least one magnetic nanoparticle, thus omitting the cumbersome experimental steps, saving the long pre-treatment time, further achieving the fast separation and enrichment, and having advantages of convenient operation and fast detection.

(3) The magnetic NAEB can be modified to have the targeting molecule being unique to the bioparticle to be detected, so as to perform the qualitative and quantitative analysis of the bioparticle to be detected, and have the advantages of the high accuracy and the unique identification.

DESCRIPTION OF THE EXEMPLARY EMBODIMENTS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

An exemplary embodiment of the present disclosure provides a magnetic NAEB, wherein at least one magnetic nanoparticle is included in a magnetic nanoaggregate with the favorable SERS characteristic, and a protective nanoshell, which is made of silica, polymer, or metal oxide such as titania and zirconia, covers the nanoparticles, thereby preventing the magnetic nanoaggregate from disintegration. Overall, the magnetic NAEB provided by the exemplary embodiment of the present disclosure has the technical results of fast magnetic separation and pre-concentration. Preferably, a chemical modification process can be performed to conjugate one or more targeting molecules (such as antibody, aptamer, DNA, glycan, or chemical group) on the outer wall of the protective nanoshell, wherein the targeting molecules correspond to the surface functionality of the bioparticles to be detected. Thus, the magnetic NAEB has characteristics of biostability, biocompatibility and unique binding.

Additionally, in the exemplary embodiment of the present disclosure, the filtering membrane can filter bioparticles bound with the magnetic NAEBs, so as to leave the filtered bioparticles on the filtering membrane. Then, a Raman microscope is used to observe a SERS spectrum of the magnetic NAEBs which are bound to the bioparticles and left on the filtering membrane, so as to detect the bioparticles. Furthermore, another one exemplary embodiment of the present disclosure provides a manufacturing method of magnetic NAEBs.

Figure 1:
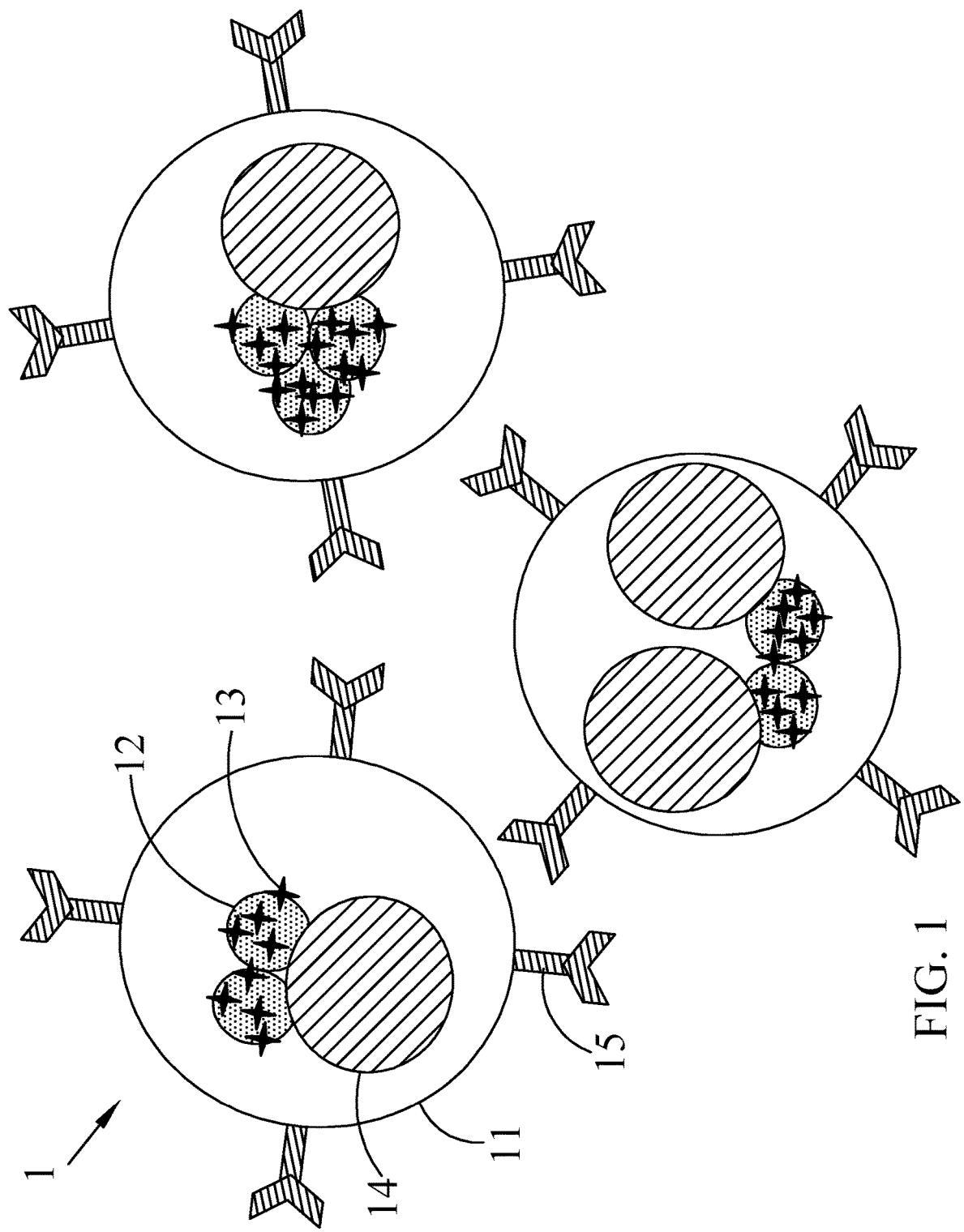
FIG. 1 is a schematic diagram of a composition of magnetic NAEBs according to one exemplary embodiment of the present disclosure.

Firstly, referring to FIG. 1, FIG. 1 is a schematic diagram of a composition of the magnetic NAEBs according to one exemplary embodiment of the present disclosure. Each of the magnetic NAEBs 1 in FIG. 1 comprises a protective nanoshell 11, noble metal nanoparticles 12, Raman reporter molecules 13, one or more magnetic nanoparticles 14 and targeting molecules 15. The protective nanoshell 11 is made of a silica, polymer, or metal oxide such as titania and zirconia, and the present disclosure is not limited thereto. The noble metal nanoparticles can be gold nanoparticles or silver nanoparticles. The protective nanoshell 11 is used to cover the magnetic nanoaggregate formed by the noble metal nanoparticles 12, the Raman reporter molecules 13 and the at least one magnetic nanoparticle 14, so as to prevent the magnetic nanoaggregate from disintegration.

In addition, the targeting molecule 15 is conjugated on the outer wall of the protective nanoshell 11 by performing a chemical modification, wherein the type of the targeting molecule 15 corresponds to the type of the surface functionality on the bioparticle where the bound magnetic NAEB 1 is dedicated for detection. The targeting molecule 15 can be antibody, aptamer, DNA, glycan, or chemical group, and the present disclosure is not limited thereto. It is noted that the targeting molecule 15 is not the essential component of the magnetic NAEB 1 provided by the exemplary embodiment of the present disclosure, and that is in some applications, the magnetic NAEB 1 does not has the targeting molecule 15.

In the exemplary embodiment of the present disclosure, through the control of the concentration of the Raman reporter molecules 13 in the solution and the pH value of the solution, the noble metal nanoparticles 12 are attracted by the Raman reporter molecules 13 to aggregate, wherein the number of the noble metal nanoparticles 12 is about 3-5, the noble metal nanoparticles 12 have an average diameter of about 5 nm-40 nm, for example 13 nm, and the present disclosure does not limit the number and the diameter of the noble metal nanoparticles 12 in NAEB. Moreover, the Raman reporter molecules 13 can be selected from at least one of Safranin O, 5-TRITC, 5(6)XRITC, MGITC and EV, and the present disclosure is not limited thereto.

In another one implementation, the magnetic nanoparticles 14 have an average diameter of 2 nm-60 nm, for example 30 nm, and the magnetic nanoparticles 14 is a nanomagnetite with an amine group ($-NH_2$), for example a nanomonocrystalline $Fe_3O_4$, and the present disclosure does not limit the type, number, diameter and functional group of the magnetic nanoparticles 14. Since the Raman reporter molecules 13 have amine, isothiocyanate, or thiol group, and the magnetic nanoparticles 14 have the amine group, thus the attraction among the noble metal nanoparticles 12, the Raman reporter molecules 13 and the magnetic nanoparticles 14 form the magnetic nanoaggregate.

Next, referring to FIG. 2, FIG. 2 is a schematic diagram of a manufacturing method of the magnetic NAEBs according to one exemplary embodiment of the present disclosure. In FIG. 2, firstly, a colloidal solution of the noble metal nanoparticles 12 (for example, gold nanoparticles) is prepared, wherein there are several implementations for preparing the colloidal solution, and one of the implementations is illustrated as follows.

1 g $HAuCl_4$ is diluted with 1 l water, so as to produce a 2.62 mM aqueous solution of $HAuCl_4$. Next, 0.01 g $C_6H_9Na_3O_9$ is dissolved in 1 ml water, so as to produce a 1% (wt) aqueous solution of $C_6H_9Na_3O_9$. Then, 5 ml of the 2.62 mM $HAuCl_4$ solution is taken out and added in the double neck round bottom flask with 40 ml water. The double neck round bottom flask is put in the reflow device, and a magnet bar is added to stir and heat the $HAuCl_4$ solution until the $HAuCl_4$ solution boils. Next, under the boiling condition of the $HAuCl_4$ solution, 1 ml of the 1% (wt) $C_6H_9Na_3O_9$ solution is quickly added in the double neck round bottom flask, and then the resulting solution in the double neck round bottom flask is further stirred and heated for 15 minutes. Next, the solution in the double neck round bottom flask is cooled down to room temperature, and then is stored in a 4 Celsius degree icebox. Thus, the gold colloid solution is ready to be used in subsequent experiments.

Next, at step S21, an aqueous solution of the Raman reporter molecules 13 is added into the gold colloid solution, and the pH value of the gold colloid solution is adjusted, so as to make the Raman reporter molecules 13 attract to the noble metal nanoparticles 12 to generate the gold nanoaggregate. The Raman reporter molecules 13 can be Safranin O, and the details are illustrated as follows.

0.2 g NaOH is added in 50 ml water to prepare an aqueous solution of 0.1 M NaOH. Then, the $10^{-4}$ M Safranin O solution is prepared. Next, 4 ml gold colloid solution is taken out, and the 0.1 M NaOH solution is used to adjust the pH value of the gold colloid solution, wherein the pH value is adjusted to 10. Then, 30 µl of $10^{-4}$ M Safranin O solution is taken out and added in the gold colloid solution while it is rapidly stirred, and then the resulting solution is allowed to stand for 15 minutes, so as to obtain the solution of dye-induced gold nanoaggregates based on the attraction between the Raman reporter molecules 13 and the noble metal nanoparticles 12.

Next, at step S22, an aqueous solution of the magnetic nanoparticles 14 is added in the solution generated by step S21, and since one or more magnetic nanoparticles 14 can also bind to the noble metal nanoparticles 12, the noble metal nanoparticles 12, the Raman reporter molecules 13 and one or more magnetic nanoparticles 14 form the magnetic nanoaggregate. One implementation of step S22 is illustrated as follows.

The magnetic nanoparticles 14 are nano $Fe_3O_4$, for example. Firstly, the aqueous solution of nano $Fe_3O_4$ is pre-processed. The pre-processing comprises steps as follows, 120 µl aqueous solution of nano $Fe_3O_4$ with amine group is put in the centrifuge tube, a magnetic component MAG is disposed outside and below the centrifuge tube to separate the upper liquid layer and the lower liquid layer, the upper liquid layer is removed, and 120 µl water is added in the remaining lower liquid layer, so as to prepare the stock solution of nano $Fe_3O_4$. Next, 30 µl of nano $Fe_3O_4$ solution (it has 8 mg Fe per µl, and the $Fe_3O_4$ nanoparticles have an average diameter of about 30 nm) is taken out and added in the solution generated by step 21 under rapid stirring, and then the solution is allowed to stand for 15 minutes, so as to obtain the solution of magnetic nanoaggregates.

Next, at step S23, MPTMS is added in the solution generated by step S22, such that the surface of the magnetic nanoaggregates have the $—Si(OCH_3)_3$ groups. One implementation of step S23 is illustrated as follows.

1.9 µl MPTMS is taken out and dissolved in 400 µl EtOH, so as to prepare the 0.024 M MPTMS/EtOH solution. Then, 20 µl of the 0.024M MPTMS/EtOH solution is added in the solution generated by step 22 under rapid stirring, and the resulting solution is allowed to stand for 15 minutes.

Next at step S24, a sol-gel reaction of hydrolysis-condensation is performed on the surface of the MPTMS-modified magnetic nanoaggregates in the solution generated by steps S23. Therefore, the protective nanoshells 11, which is made of silica, cover the magnetic nanoaggregates, and the solution of the magnetic NAEBs 1' is obtained. One implementation of step S24 is illustrated as follows.

12.5 µl TEOS is taken out and dissolved in 1200 µl ethanol, so as to prepared 0.0046M TEOS/EtOH solution. Subsequently, 15 ml ethanol, 500 µl of 33% (wt) $NH_4OH$ solution and 150 µl of 0.0046 M TEOS/EtOH solution are sequentially added in the solution generated by step S23 rapidly, the resulting solution is then sonicated for 30 minutes. Next, 150 µl of 0.0046M TEOS/EtOH solution is added in the solution again, and the resulting solution is sonicated for 30 minutes again (the step can be repeated three times, and totally 600 µl of 0.0046M TEOS/EtOH solution are added). Then, the above solution is further sonicated for 12 hours. Next, the resulting solution after sonication is put in a centrifuge tube and centrifuged for 12 minutes at 1200 rpm speed. Then, the upper liquid layer in the centrifuge tube is removed and the lower liquid layer is kept, and ethanol is used to rinse the remaining solution by centrifugation three times. Finally, pure water is used to dilute the remaining solution to 1 ml, and the 1 ml solution is stored in a cool space at room temperature. Therefore, the magnetic nanoaggregates covered by the protective nanoshells 11 made of the silica is obtained, and the aqueous solution of the magnetic NAEBs 1' is obtained.

Figure 2:
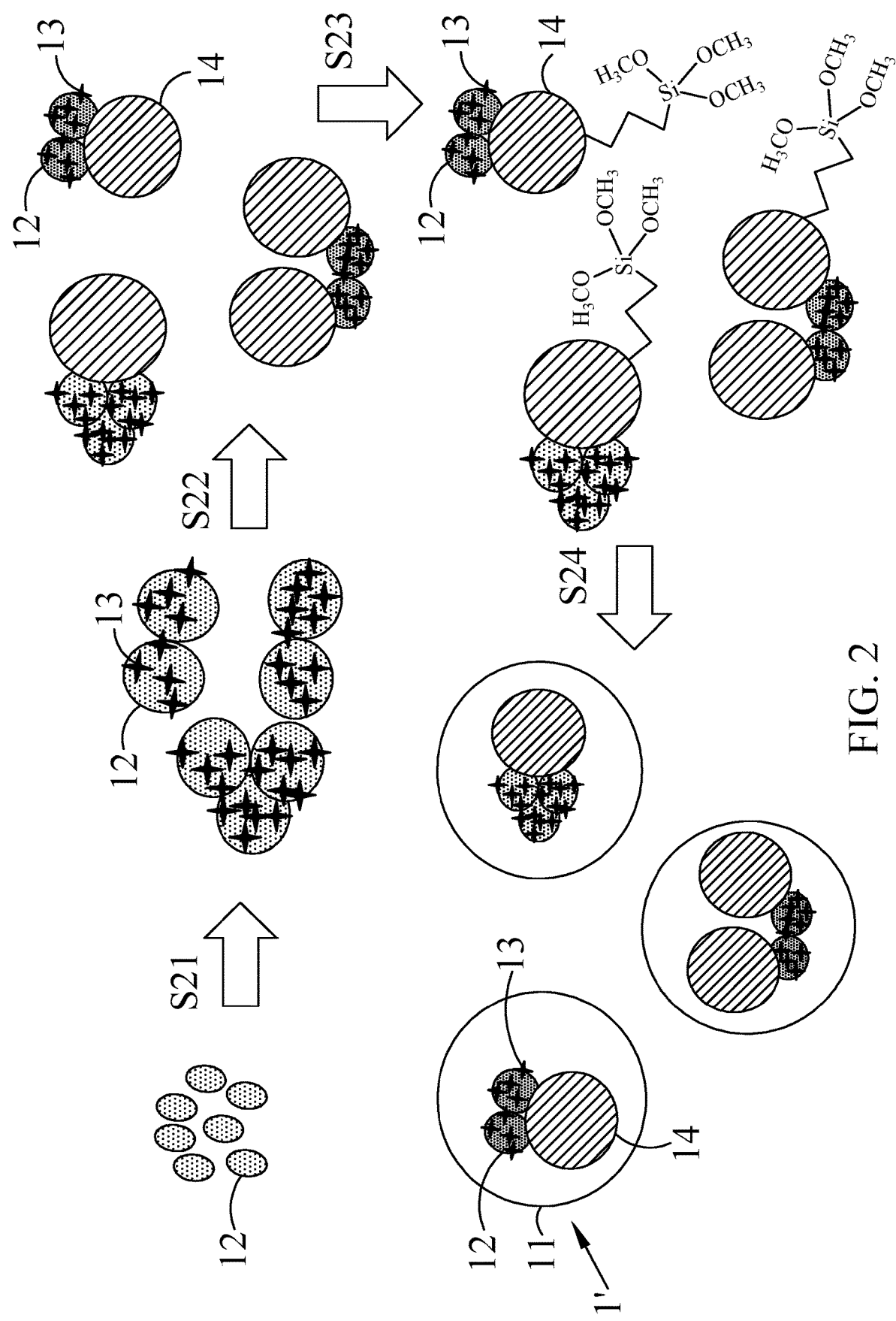
FIG. 2 is a schematic diagram of a manufacturing method of the magnetic NAEBs according to one exemplary embodiment of the present disclosure.

According to the detailed descriptions of FIG. 2, it can be known that the manufacturing method of the magnetic NAEBs 1' basically has two main steps, wherein steps S21 and S22 are used to make the noble metal nanoparticles 12, the Raman reporter molecules 13 and the at least one magnetic nanoparticle 14 to form the magnetic nanoaggregates, and then steps S23 and S24 are used to form the protective nanoshells 11 made of the silica to cover the magnetic nanoaggregates.

Figure 3:
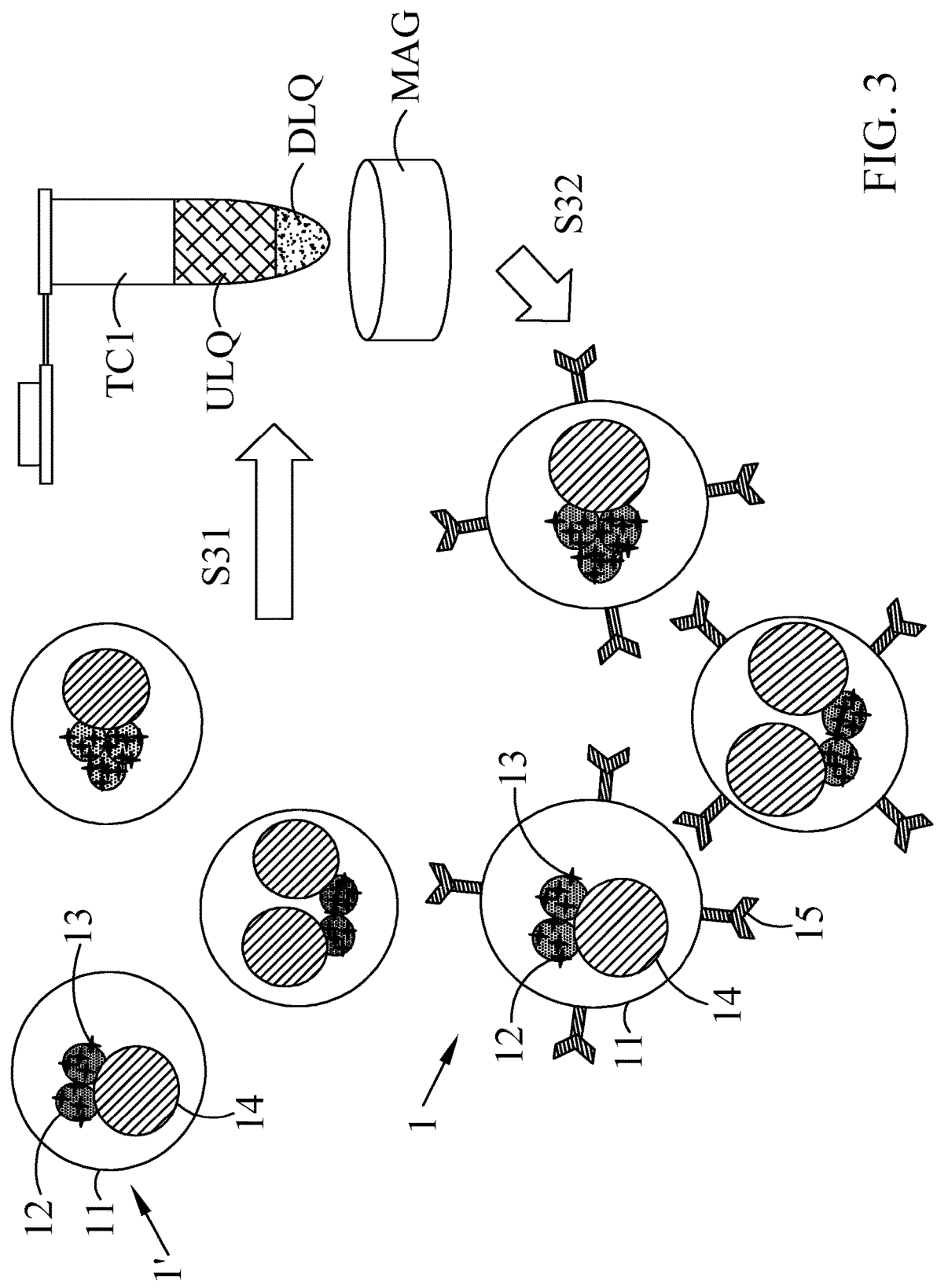
FIG. 3 is a schematic diagram which a pre-concentration process and a chemical modification process are performed on the magnetic NAEBs according to one exemplary embodiment of the present disclosure.

Next, referring to FIG. 3, FIG. 3 is a schematic diagram which a pre-concentration process and a chemical modification process are performed on the magnetic NAEBs according to one exemplary embodiment of the present disclosure. At step S31, a magnet is used to perform pre-concentration of the magnetic NAEBs 1'. One implementation of pre-concentration in step S31 is illustrated.

1 ml aqueous solution finally generated in FIG. 2 and 10 ml ethanol are put in the centrifuge tube TC1, 1 µl APTES is added in the solution, and the solution is stirred for 12 hours. Next, the solution in the centrifuge tube TC1 is heated to 50 Celsius degree, then, the solution is stirred for 1 hour, and cooled down to room temperature. Next, ethanol is used to rinse the solution at 10000 rps for 10 minutes. The rinsing process is performed three times to remove the upper liquid layer. After the upper liquid layer is removed, PBS buffer is added to make the solution to 1 ml. Next, the magnetic component MAG is used to collect the magnetic NAEBs 1' by removing the upper liquid layer ULQ in the centrifuge tube TC1, and keeping the lower liquid layer DLQ with the magnetic NAEBs 1'. Then, PBS buffer is added to make the solution to 1 ml.

Next, at step S32, a chemical modification process is performed on the magnetic NAEBs 1', so as to conjugate the targeting molecules 15 on the outer walls of the protective nanoshells 11. Therefore, the functionalized magnetic NAEBs 1 are obtained. One implementation of the chemical modification at step S32 is illustrated as follows.

The 1 ml solution obtained by step S31 is separated to five parts (each is 200 µl), and 40 µl antibody solution and 20 µl EDC/NHS solution are added and dissolved in the 200 µl solution. Then, the 200 µl solution is sonicated for 2 hours at room temperature. The above antibody solution is prepared in PBS buffer to have a concentration of $5\times10^{-6}$ g per ml. The above EDC/NHS solution is prepared by dissolving EDC and NHS in PBS buffer, wherein the EDC/NHS solution has 0.523 M EDC and 0.869 M NHS. Next, 500 µl of 10 mM quench buffer solution is added, and the resulting solution is allowed to react for 30 minutes at room temperature. The above quench buffer is prepared by dissolving 20 µl monoethanolamine in 1980 µl pure water to have a concentration of 10 mM. Next, PBS buffer is used to rinse the solution for 10 minutes at 10000 rps. The rinsing process is performed three times to remove the upper liquid layer. After the the upper liquid layer is removed, PBS buffer is added to make the solution to 11 ml, and thus the solution of magnetic NAEBs 1 is obtained. Preferably, the obtained solution can be preserved in a 4 Celsius degree icebox.

Figure 4:
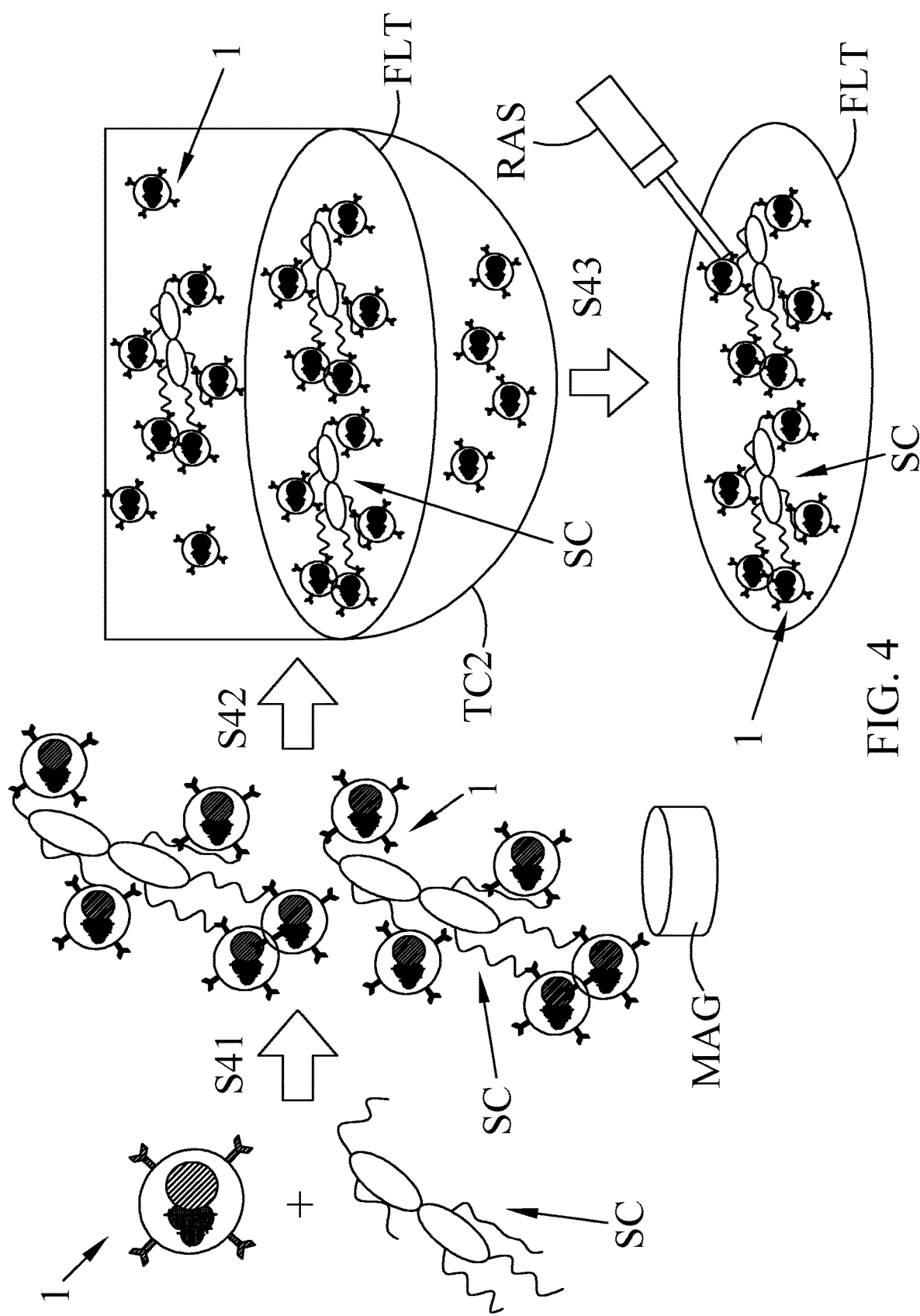
FIG. 4 is a schematic diagram of a bioparticle detection method using the magnetic NAEBs according to one exemplary embodiment of the present disclosure.

Next, referring to FIG. 4, FIG. 4 is a schematic diagram of a bioparticle detection method using the magnetic NAEBs according to one exemplary embodiment of the present disclosure. The bioparticles in FIG. 4 are *Salmonella* SC, for example. The targeting modules of the magnetic NAEBs 1 are antibody molecules having specific affinity for the *Salmonella* SC, the filtering membrane FLT has pores of 0.45 µm in average diameter, and the present disclosure is not limited thereto. The pore diameter of the filtering membrane FLT should be larger than the average diameter of the magnetic NAEBs 1 and less than the width of the *Salmonella* SC, wherein the length and width of the *Salmonella* SC are generally about 1 µm-3 µm and 0.6 µm-0.9 µm, respectively, and the average diameter of the magnetic NAEBs 1 is about 80 nm-200 nm, and thus the average pore diameter of the filtering membrane FLT can be between 0.25 µm and 0.55 µm. Firstly, at step S41, the magnetic NAEBs 1 bind to the *Salmonella* SC, and a magnetic component MAG (such as a magnet) is used to attract the magnetic NAEBs 1 with bound *Salmonella* SC and the free magnetic NAEBs 1 to move to the MAG for pre-concentration.

Next, at step S42, the filtering membrane FLT is put in the centrifuge tube TC2, and through centrifugation, the one or more bound bioparticles are attracted by the magnetic component MAG and left on the filtering membrane FLT, while the unbound magnetic NAEBs 1 pass through the filtering membrane FLT. Next, at step S43, the filtering membrane FLT is taken out, and the Raman microscope RAS (such as confocal Raman microscope) is used to observe a SERS spectrum of the magnetic NAEBs 1 with bound *Salmonella* SC left on the filtering membrane, so as to detect the *Salmonella* SC.

If no *Salmonella* SC are bound with the magnetic NAEBs 1, all of the magnetic NAEBs 1 will pass through the filtering membrane FLT, and thus the SERS spectrum of the magnetic NAEBs 1 cannot be observed by the Raman microscope RAS. By contrast, if there are *Salmonella* SC bound with the magnetic NAEBs 1 and left on the filtering membrane FLT, the SERS spectrum of the one or more magnetic NAEBs 1 on the filtering membrane FLT can be observed by the Raman microscope RAS, so as determine whether the *Salmonella* SC exist, and further to determine the concentration of the *Salmonella* SC.

Figure 5:
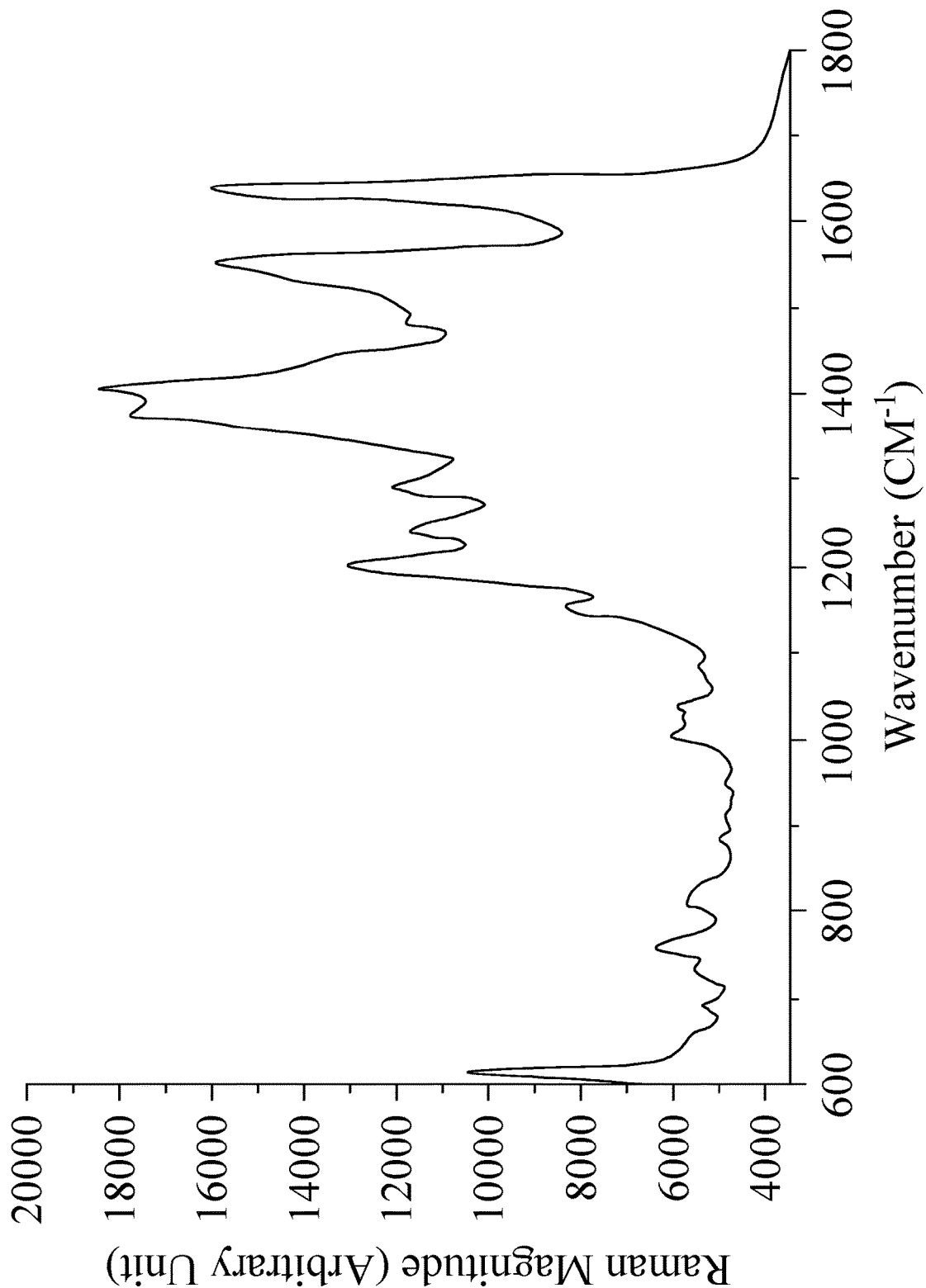
FIG. 5 is a spectrum diagram of a SERS spectrum of the magnetic NAEBs according to one exemplary embodiment of the present disclosure.
Figure 6:
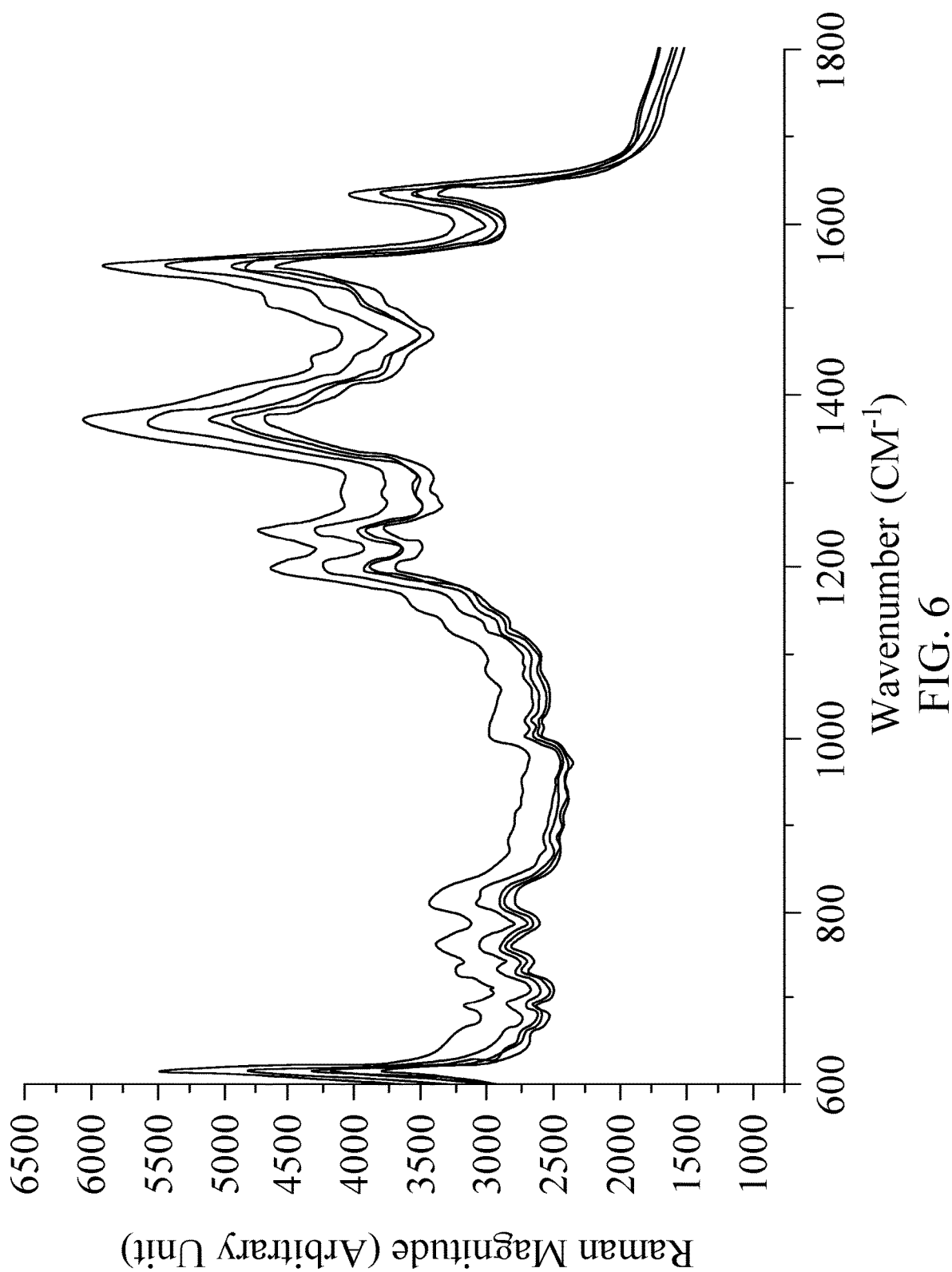
FIG. 6 is a spectrum diagram of a SERS spectrum of the magnetic NAEBs bound to the *Salmonella* according to one exemplary embodiment of the present disclosure.

Next, referring to FIG. 5 and FIG. 6, FIG. 5 is a spectrum diagram of a SERS spectrum of the magnetic NAEBs according to one exemplary embodiment of the present disclosure, and FIG. 6 is a spectrum diagram of a SERS spectrum of the magnetic NAEBs bound to the *Salmonella* SC according to one exemplary embodiment of the present disclosure, wherein the X-axis represents the wavenumber ($cm^{-1}$), and the Y-axis represents the Raman intensity (using the arbitrary unit for relative intensity). The five curves in FIG. 6 shows the SERS spectra of five arbitrary samples (which have the magnetic NAEBs 1 bound to the *Salmonella* SC) on the filtering membrane FLT in FIG. 4, after the laser beam illuminates the five arbitrary samples. In the exemplary embodiment, the magnetic NAEBs 1 bind to the *Salmonella* SC, the SERS spectrum has insignificant difference as compared to that of the free magnetic NAEBs 1 as shown in FIG. 5. In addition, the shape and intensity of the SERS spectra in FIG. 6 obtained at different locations of the filtering membrane FLT have little differences. Specifically, a peak occurs at 1553 wavenumber in FIG. 5, and a peak also occurs at 1553 wavenumber in FIG. 6. Therefore, it demonstrates that the filtering membrane FLT in FIG. 4 has the magnetic NAEBs 1 bound to the *Salmonella* SC.

Figure 7:
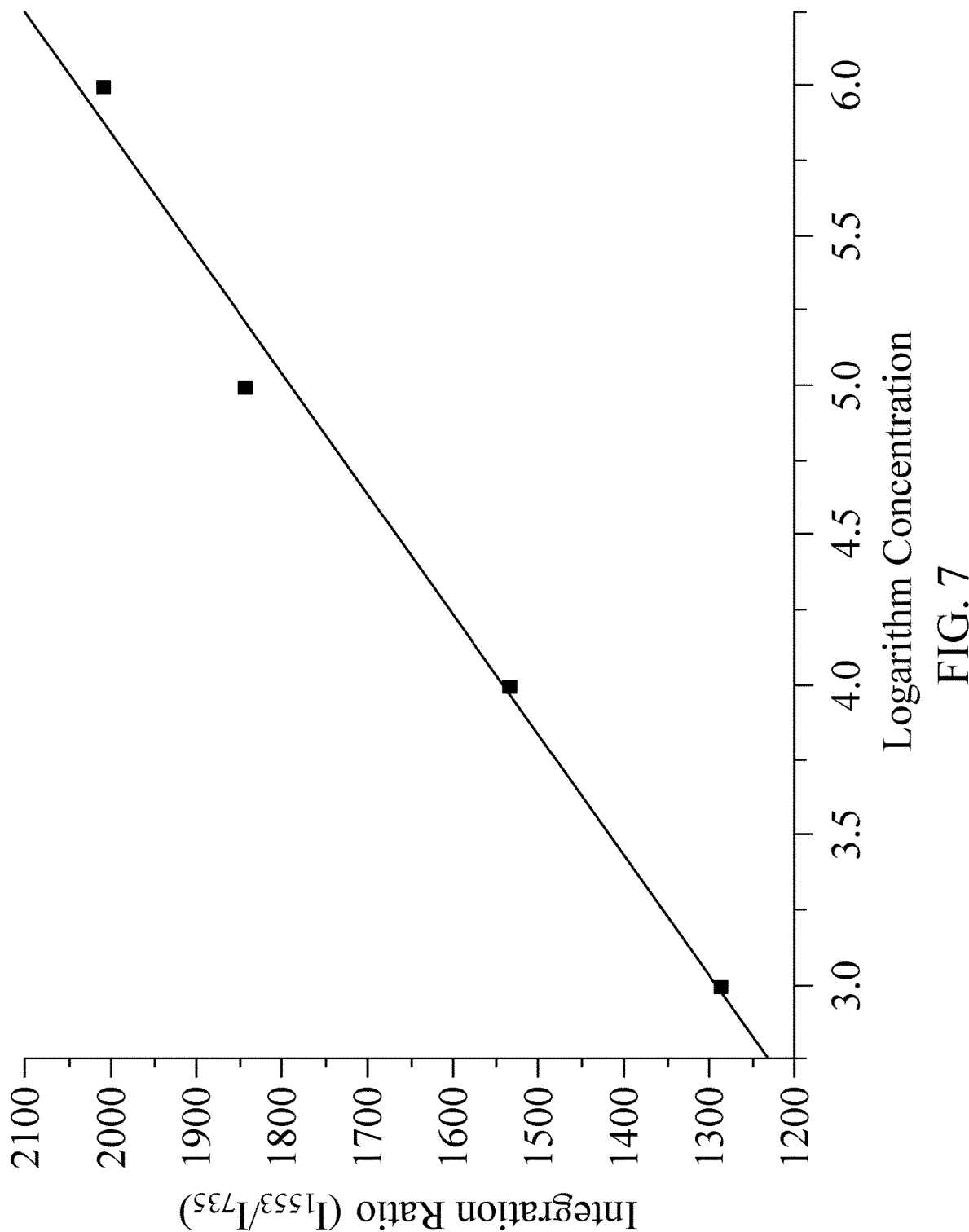
FIG. 7 is a diagram showing a plot of the intensity ratio at two specific wavenumbers versus the logarithm concentration of the *Salmonella* after the magnetic NAEBs are bound to the *Salmonella* according to one exemplary embodiment of the present disclosure.

Finally, referring to FIG. 7, FIG. 7 is a diagram showing a plot of the intensity ratio at two specific wavenumbers versus the logarithm concentration of the *Salmonella* SC after the magnetic NAEBs are bound to the *Salmonella* SC according to one exemplary embodiment of the present disclosure. In FIG. 7, the intensity $I_{735}$ is the integrated intensity of the SERS signal at 735 wavenumber and the intensity $I_{1553}$ is the integrated intensity at 1553 wavenumber. After the magnetic NAEB bound to the *Salmonella* SC, the SERS intensity at 735 wavenumber is not affected by the concentration of *Salmonella* SC, but the SERS intensity at 1553 wavenumber obviously varies with the concentration of *Salmonella* SC. With samples of four different concentrations of the *Salmonella* SC, a plot of the measured intensity ratio $I_{1553}/I_{735}$ at 735 and 1553 wavenumbers versus the logarithm concentration of the *Salmonella* SC is shown in FIG. 7. Furthermore, by the linear regression, the linear fitted line can be obtained, such that it can be demonstrated that the intensity ratio $I_{1553}/I_{735}$ is proportional to the logarithm concentration of the *Salmonella* SC.

Accordingly, the magnetic NAEB provided by the exemplary embodiment of the present disclosure can be used in the bioparticle detection method, and thus the bioparticle detection method has advantages of low cost, convenient operation, fast detection, and high accuracy.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A magnetic nanoaggregate-embedded bead (NAEB), comprising:
    a protective nanoshell;
    noble metal nanoparticles;
    Raman reporter molecules; and at least one magnetic nanoparticle;
    wherein the protective nanoshell covers the noble metal nanoparticles, the Raman reporter molecules and the at least one magnetic nanoparticle, and the noble metal nanoparticles, the Raman reporter molecules and the at least one magnetic nanoparticle form a magnetic nanoaggregate,
    wherein the at least one magnetic nanoparticle is a nanomagnetite with an —$NH_2$ amine group.

2. The magnetic NAEB according to claim 1, wherein the noble metal nanoparticles are gold nanoparticles or silver nanoparticles.

3. The magnetic NAEB according to claim 1, further comprising:
    at least one targeting molecule, formed at an outer wall of the protective nanoshell, wherein a type of the targeting molecule corresponds to a type of a bioparticle to be detected.

4. The magnetic NAEB according to claim 2, wherein the magnetic nanoparticle has a diameter of 2 nm-60 nm, and the gold nanoparticle has a diameter of 5 nm-40 nm.

5. The magnetic NAEB according to claim 1, wherein the protective nanoshell is made of silica, polymer, or metal oxide.

6. The magnetic NAEB according to claim 1, wherein the Raman reporter molecules are selected from at least one of Safranin O, 5-TRITC, 5(6)XRITC, MGITC and EV.

7. The magnetic NAEB according to claim 3, wherein the targeting molecule is an antibody, an aptamer, a DNA, a glycan, or a chemical group.

8. A manufacturing method of magnetic nanoaggregate-embedded beads (NAEBs), comprising:
   making noble metal nanoparticles, Raman reporter molecules and magnetic nanoparticles to form magnetic nanoaggregates; and
   forming protective nanoshells to cover the magnetic nanoaggregates,
   wherein the at least one magnetic nanoparticle is a nanomagnetite with an —$NH_2$ amine group.

9. The manufacturing method of the magnetic NAEBs according to claim 8, further comprising the utilization of a magnetic component to perform a pre-concentration process on the magnetic NAEBs.

10. A bioparticle detection method using magnetic nanoaggregate-embedded beads (NAEBs), comprising:
    providing the magnetic NAEBs, wherein each of the magnetic NAEBs comprises a protective nanoshell, noble metal nanoparticles, Raman reporter molecules and at least one magnetic nanoparticle, wherein the protective nanoshell covers the noble metal nanoparticles, the Raman reporter molecules and the at least one magnetic nanoparticle, and the noble metal nanoparticles, the Raman reporter molecules and the least one magnetic nanoparticle form a magnetic nanoaggregate;
    making the magnetic NAEBs bind to one or more bioparticles;
    utilizing a magnetic component to attract the bioparticles bound with the magnetic NAEBs and the unbound magnetic NAEBs;
    utilizing a filtering membrane to filter the bioparticles which are bound with the magnetic NAEBs and attracted by the magnetic component, so as to leave the filtered bioparticles on the filtering membrane; and
    utilizing a Raman microscope to observe a surface-enhanced Raman scattering (SERS) spectrum of the magnetic NAEBs which are bound to the bioparticles and left on the filtering membrane, so as to detect the bioparticles,
    wherein the at least one magnetic nanoparticle is a nanomagnetite with an —$NH_2$ amine group.

11. The bioparticle detection method using the magnetic NAEBs according to claim 10, wherein the bioparticles are bacteria, virus, or cell.

12. The bioparticle detection method using the magnetic NAEBs according to claim 10, wherein the bioparticles are *Salmonella*, and the filtering membrane has pores with an average diameter of 0.25 μm-0.55 μm.

13. The bioparticle detection method using the magnetic NAEBs according to claim 10, wherein each of the magnetic NAEBs further comprises at least one targeting molecule, formed at an outer wall of the protective nanoshell, wherein a type of the targeting molecule corresponds to a type of a bioparticle to be detected.

14. The bioparticle detection method using the magnetic NAEBs according to claim 10, wherein the noble metal nanoparticles are gold nanoparticles or silver nanoparticles.

15. The bioparticle detection method using the magnetic NAEBs according to claim 10, wherein the protective nanoshell is made of silica, polymer, or metal oxide.

16. The bioparticle detection method using the magnetic NAEBs according to claim 14, wherein the magnetic nanoparticle has a diameter of 2 nm-60 nm, and the gold nanoparticle has a diameter of 5 nm-40 nm.

17. The bioparticle detection method using the magnetic NAEBs according to claim 10, wherein the Raman reporter molecules are selected from at least one of Safranin O, 5-TRITC, 5(6)XRITC, MGITC and EV.

18. The bioparticle detection method using the magnetic NAEBs according to claim 13, the targeting molecule is an antibody, an aptamer, a DNA, a glycan, or a chemical group.

* * * * *